US008871496B1

(12) United States Patent
Sommer et al.

(10) Patent No.: US 8,871,496 B1
(45) Date of Patent: Oct. 28, 2014

(54) METHODS, MICROFLUIDIC DEVICES, AND SYSTEMS FOR DETECTION OF AN ACTIVE ENZYMATIC AGENT

(75) Inventors: Gregory J. Sommer, Livermore, CA (US); Anson V. Hatch, Tracy, CA (US); Anup K. Singh, Danville, CA (US); Ying-Chih Wang, Pleasanton, CA (US)

(73) Assignee: Sandia Corporation, Albuquerque, NM (US)

( * ) Notice: Subject to any disclaimer, the term of this patent is extended or adjusted under 35 U.S.C. 154(b) by 928 days.

(21) Appl. No.: 12/544,982

(22) Filed: Aug. 20, 2009

(51) Int. Cl.
*C12M 1/34* (2006.01)
*C12M 3/00* (2006.01)

(52) U.S. Cl.
USPC ......... 435/287.2; 435/287.3; 435/23; 436/43; 436/63; 436/4; 436/518; 422/68.1; 422/81; 422/82

(58) Field of Classification Search
USPC .......... 435/288.7, 23, 287.3, 287.2; 422/68.1, 422/81, 82; 436/4, 43, 63, 518
See application file for complete search history.

(56) References Cited

U.S. PATENT DOCUMENTS

| | | | |
|---|---|---|---|
| 6,221,677 B1 * | 4/2001 | Wu et al. ....................... | 436/518 |
| 6,488,872 B1 | 12/2002 | Beebe | |
| 2004/0009489 A1 | 1/2004 | Golub | |
| 2004/0048360 A1 * | 3/2004 | Wada et al. ................ | 435/287.2 |

OTHER PUBLICATIONS

A. S. Rathore; Cs. Horvath; "Axial Nonuniformities and Flow in Columns for Capillary Electrochromatography", Analytical Chemistry, 1998, 70, pp. 3069-3077.

L. J. Jin; B. C. Giordano; J. P. Landers; "Dynamic Labeling During Capillary or Microchip Electrophoresis for Laser-Induced Fluorescence Detection of Protein-SDS Complexes Without Pre- or Postcolumn Labeling", Analytical Chemistry, 2001, 73, pp. 4994-4999.

B. S. Broyles; S. C. Jacobsen; J. M. Ramsey; "Sample Filtration, Concentration, and Separation Integrated on Microfluidic Devices", Analytical Chemistry, 2003, 75, pp. 2761-2767.

T. Vilkner; D. Janasek; A. Manz; "Micro Total Analysis Systems. Recent Developments", Analytical Chemistry, 2004, 76, pp. 3373-3386.

A. V. Hatch; A. E. Herr; D. J. Throckmorton; J. S. Brennan; A. K. Singh; "Integrated Preconcentration SDS-PAGE of Proteins in Microchips Using Photopatterned Cross-Linked Polyacrylamide Gels", Analytical Chemistry, 2006, 78, pp. 4976-4984.

C. Yu; M. H. Davey; F. Svec; J. M. J. Frechet; "Monolithic Porous Polymer for On-Chip Solid-Phase Extraction and Preconcentration Prepared by Photoinitiated in Situ Polymerization within a Microfluidic Device", Analytical Chemistry, 2001, 73, pp. 5088-5096.

(Continued)

*Primary Examiner* — William H Beisner
*Assistant Examiner* — Danielle Henkel
(74) *Attorney, Agent, or Firm* — Dorsey & Whitney LLP

(57) ABSTRACT

Embodiments of the present invention provide methods, microfluidic devices, and systems for the detection of an active target agent in a fluid sample. A substrate molecule is used that contains a sequence which may cleave in the presence of an active target agent. A SNAP25 sequence is described, for example, that may be cleaved in the presence of Botulinum Neurotoxin. The substrate molecule includes a reporter moiety. The substrate molecule is exposed to the sample, and resulting reaction products separated using electrophoretic separation. The elution time of the reporter moiety may be utilized to identify the presence or absence of the active target agent.

15 Claims, 10 Drawing Sheets

(56) References Cited

OTHER PUBLICATIONS

F. Helferich; "Ligand Exchange. II. Separation of Ligands Having Different Coordinate Valences", Journal of the American Chemical Society, 1962, 84, pp. 3242-3245.

A E. Herr; A. V. Hatch; D. J. Throckmorton; H. M. Tran; J. S. Brennan; W. V. Giannobile; A. K. Singh; "Microfluidic immunoassays as rapid saliva-based clinical diagnostics", Proceedings of the National Academy of Sciences, 2007, 104(13), pp. 5268-5273.

M. M. Chui; R. J. Phillips; M. J. McCarthy; "Measurement of the Porous Microstructure of Hydrogels by Nuclear Magnetic Resonance", Journal of Colloid and Interface Science, 1995, 174, pp. 336-344.

J. Han; A. K. Singh; "Rapid protein separations in ultra-short microchannels: microchip sodium dodecyl sulfate-polyacrylamide gel electrophoresis and isoelectric focusing", Journal of Chromatography A, 2004, 1049. pp. 205-209.

J. Khandurina; S. C. Jacobson; L. C. Waters; R. S. Foote; J. M. Ramsey; "Microfabricated Porous Membrane Structure for Sample Concentration and Electrophoretic Analysis", Analytical Chemistry, 1999, 71, pp. 1815-1819.

Y. Liu, R. S. Foote; S. C. Jacobson; R. S. Ramsey; J. M. Ramsey; "Electrophoretic Separation of Proteins on a Microchip with Noncovalent, Postcolumn Labeling", Analytical Chemistry, 2000, 72, pp. 4608-4613.

D. R. Reyes; D. Iossifidis; P-A. Auroux; A. Manz; "Micro Total Analysis Systems. 1. Introduction, Theory, and Technology", Analytical Chemistry, 2002, 74, pp. 2623-2636.

P-A. Auroux; D. Iossifidis; D. R. Reyes; A. Manz; "Micro Total Analysis Systems. 2. Analytical Standard Operations and Applications", Analytical Chemistry, 2002, 74, pp. 2637-2652.

D. J. Throckmorton; T. J. Shepodd; A. K. Singh; "Electrochromatography in Microchips: Reversed-Phase Separation of Peptides and Amino Acids Using Photopatterned Rigid Polymer Monoliths", Analytical Chemistry, 2002, 74, pp. 784-789.

A. E. Herr; A. K. Singh; "Photopolymerized Cross-Linked Polyacrylamide Gels for On-Chip Protein Sizing", Analytical Chemistry, 2004. 76, pp. 4727-4733.

S. Song; A. K. Singh; T. J. Shepodd; B. J. Kirby; "Microchip Dialysis of Proteins Using In Situ Photopatterned Nanoporous Polymer Membranes", Analytical Chemistry, 2004, 76, pp. 2367-2373.

S. Song; A. K. SiNGH; B. J. Kirby; "Electrophoretic Concentration of Proteins at Laser-Patterned Nanoporous Membranes in Microchips", Analytical Chemistry, 2004, 76, pp. 4589-4592.

G. J. Sommer; A. K. Singh; A. V. Hatch; "On-Chip Isoelectric Focusing Using Photopolymerized Immobilized pH Gradients", Analytical Chemistry, 2008, 80, pp. 3327-3333.

K. T. Haraldsson; J. B. Hutchison; R. P. Sebra; B. T. Good; K. S. Anseth; C. N. Bowman; "3D polymeric microfluidic device fabrication via contact liquid photolithographic polymerization (CLiPP)", Sensors and Actuators B, 2006, 113, pp. 454-460.

K. Chon; J. Moon; S. Kim; S-D. Kim; J. Cho; "Bio-particle separation using microfluidic porous plug for environmental monitoring", Desalination, 2007, 202, pp. 215-223.

A. L. Purcell; H. M. Hoard-Fruchey; "A capillary electrophoresis method to assay catalytic activity of botulinum neurotoxin serotypes: Implications for substrate specificity", Analytical Biochemistry, 2007, 366, pp. 207-217.

S. Chen; C. Hall; J. T. Barbieri; "Substrate Recognition of VAMP-2 by Botulinum Neurotoxin B and Tetanus Neurotoxin", Journal of Biological Chemistry, 2008, 283(30), pp. 21153-21159.
N.B. Cramer; S. K. Reddy; M. Cole; C. Hoyle; C. N. Bowman; "Initiation and Kinetics of Thiol-ene Photopolymerizations without Photoinitiators", Journal of Polymer Science: Part A: Polymer Chemistry, 2004, 42, pp. 5817-5826.
J. B. Hutchison; K. T. Haraldsson; B. T. Good; R. P. Sebra; N. Luo; K. S. Anseth; C. N. Bowman; "Robust polymer microfluidic device fabrication via contact liquid photolithographic polymerization (CLiPP)", Lab Chip, 2004, 4, pp. 658-662.
H. M. Simms; C. M. Brotherton; B. T. Good; R. H. Davis; K. S. Anseth; C. N. Bowman; "In situ fabrication of macroporous polymer networks within microfluidic devices by living radical photopolymerization and leaching", Lab Chip, 2005, 5, pp. 151-157.
G. V. Zilberstein; E. M. Baskin; S. Bukshpan; L. E. Korol; "Parallel isoelectric foccusing II", Electrophoresis, 2004, 25, pp. 3643-3651.
J. Moorthy; G. A. Mensing; D. Kim; S. Mohanty; D. T. Eddington; W. H. Tepp; E. A. Johnson; D. J. Beebe; "Microfluidic tectonics platform: A colorimetric, disposable botulinum toxin enzyme-linked immunosorbent assay system", Electrophoresis 2004, 25, pp. 1705-1713.
K. Kleparnik; P. Mikuska; "A Continuous-flow instrument for the determination of linear polyacrylamide stability", Electrophoresis 2004, 25, pp. 2139-2143.
P. Lim; R. North; G. Vigh; "Rapid isoelectric trapping in a micropreparative-scale multicompartment electrolyzer", Electrophoresis 2007, 28, pp. 1851-1859.
Invitrogen Life Technologies, Instruction Manual, ZOOM IEF Fractionator, Cat. Nos. ZF10001 & ZF10002, Version C, Jul. 2004, pp. 1-64.
D. Fologea; M. Gershow; B. Ledden; D. S. McNabb; J. A. Golovchenko; J. Li; "Detecting Single Stranded DNA with a Solid State Nanopore", Nano Letters, 2005, 5(10), pp. 1905-1909.
D. Figeys; N. J. Dovichi; "Multiple Separations of DNA sequencing fragments with a non-cross-linked polyacrylamide-filled capillary: capillary electrophoresis at 300 V/cm", Journal of Chromatography A, 1995, 717, pp. 113-116.
D. J. Beebe; J. S. Moore, Q. Yu; R. H. Liu; M. L. Kraft; B-H. Jo; C. Devadoss, "Microfluidic tectonics: A comprehensive construction platform for microfluidic systems", Proceedings of the National Academy of Sciences, 2000, 97(25), pp. 13488-13493.
K. Swinney; D. J. Bornhop; "Detection in capillary electrophoresis", Electrophoresis 2000, 21, pp. 1239-1250.
S. H. Brahmasandra; V. M. Ugaz; D. T. Burke; C. H. Mastrangelo; M. A. Burns; "Electrophoresis in microfabricated devices using photopolymerized polyacrylamide gels and electrode-defined sample injection", Electrophoresis 2001, 22, pp. 300-311.
C. R. Cabrera; P. Yager; "Continuous concentration of bacteria in a microfluidic flow cell using electrokinetic techniques", Electrophoresis 2001, 22, pp. 355-362.
T. Huang; J. Pawliszyn; "Microfabrication of a tapered channel for isoelectric focusing with thermally generated pH gradient", Electrophoreis 2002, 23, pp. 3504-3510.
A B. Jemere; R. D. Oleschuk; F. Ouchen; F. Fajuyigbe; D. J. Harrison; "An integrated soiid-phase extraction system for sub-picomolar detection", Electrophoresis 2002, 23, pp. 3537-3544.
C. Khoury; G. A. Mensing; D. J. Beebe; "Ultra rapid prototyping of microfluidic systems using liquid phase photopolymerization", Lab on a Chip, 2002, 2, pp. 50-55.
D. Ogle; A. Ho; T. Gibson; D. Rylatt; E. Shave; P. Lim; G. Vigh; "Preparative-scale isoelectric trapping separations using a modified Gradiflow unit", Journal of Chromatography A, 2002, 979, pp. 155-161.
A. Wainright; S. J. Williams; G. Ciambrone; Q. Xue; J. Wei; D. Harris; "Sample pre-concentration by isotachophoresis in microfluidic devices", Journal of Chromatography A, 2002), 979, pp. 69-80.
G. V. Zilberstein; E. M. Baskin; S. Bukshpan; "Parallel processing in the isoelectric focusing chip", Electrophoresis 2003, 24, pp. 3735-3744.
O. Bilenko; D. Gavrilov; B. Gorbovitski; V. Gorfinkel; M. Gouzman; G. Gudkov; V. Khozikov; O. Khozikov; O. Kosobokova; N. Lifshitz; S. Luryi; A. Stepoukhovitch; M. Tcherevishinick; G. Tyshko; "Formation of a resistive region at the anode end in DNA capillary electrophoresis", Electrophoresis 2003, 24, pp. 1176-1183.
Y. Li; D. L. Devoe; C. S. Lee; "Dynamic analyte introduction and focusing in plastic microfluidic devices for proteomic analysis", Electrophoresis 2003, 24, pp. 193-199.

* cited by examiner

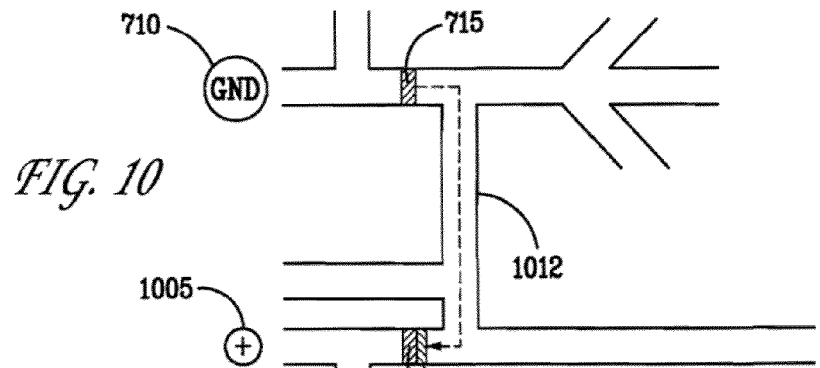
FIG. 10
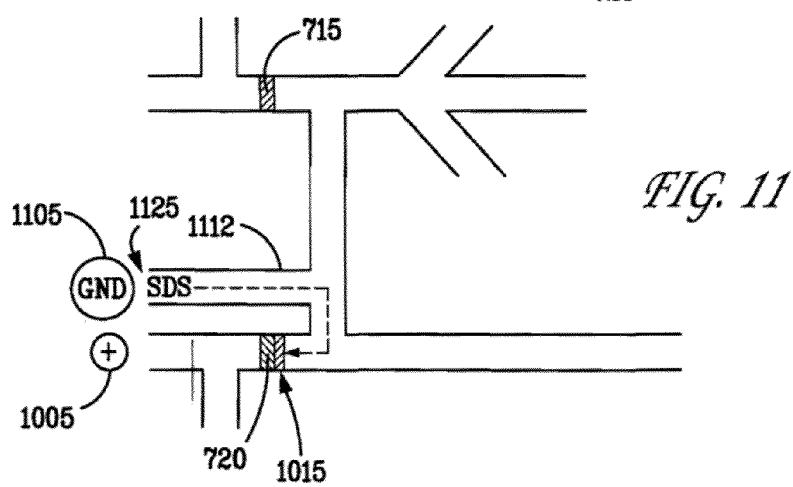
FIG. 11
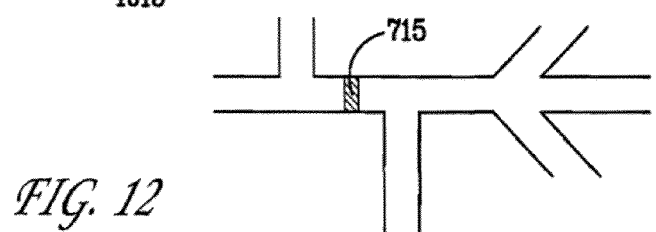
FIG. 12
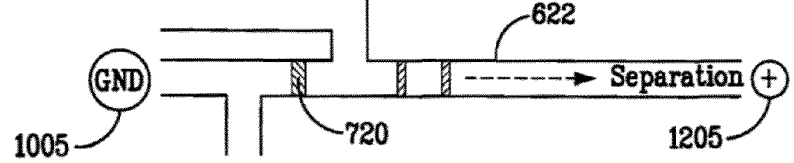

SEQUENCE LISTING

<160> NUMBER OF SEQ ID NOS: 1

<210> SEQ ID NO 1
<211> LENGTH: 206
<212> TYPE: PRT
<213> ORGANISM: Homo sapiens

<400> SEQUENCE: 1

```
Met Ala Glu Asp Ala Asp Met Arg Asn Glu Leu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Asp Arg Val Glu Glu Gly Met
        50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
                180                 185                 190
```

```
Asp Glu Ala Asn Gln Arg Ala Thr Lys Met Leu Gly Ser Gly
        195                 200                 205
```

METHODS, MICROFLUIDIC DEVICES, AND SYSTEMS FOR DETECTION OF AN ACTIVE ENZYMATIC AGENT

STATEMENT REGARDING RESEARCH & DEVELOPMENT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

TECHNICAL FIELD

Embodiments of the invention relate generally to enzymatic activity assays and microfluidic devices for performing biological assays.

BACKGROUND

Botulinum Neurotoxin (BoNT) is a category A select agent with extreme potency (lethal dose of ~1 ng/kg in humans). Upon infection, BoNT impairs neuronal synaptic transmission in the peripheral nervous system, which may lead to paralysis and eventual respiratory failure. The toxin has seven serotypes (A-G), each consisting of a heavy chain (Hc, 100 kDa) and a light chain (Lc, 50 kDa). The heavy chain enables binding of the toxin to neuronal cell surface receptors and induces translocation of the light chain across the cell membrane. Once inside the cell, the enzymatic light chain cleaves a specific peptide sequence in one of the three soluble N-ethylmaleimide-sensitive factor attachment protein receptor (SNARE) proteins, thereby inhibiting acetylcholine release and impairing neuronal function. Serotype A (BoNT/A), the most common variant found in human cases, cleaves the synaptosome-associated protein of 25 kDa (SNAP-25) within the SNARE complex. Information about Botulinum Neurotoxin A may be found in Cai, S., Singh, B. R., *Critical Reviews in Microbiology*, 33 (2007): 109-125, which is hereby incorporated by reference for any purpose. Serotypes C and E (BoNT/C and BoNT/E) also cleave SNAP-25 at other sites. VAMP-2 is another SNARE protein, and is cleaved by BoNT/B, BoNT/D, BoNT/F and BoNT/G at different sites. Information about VAMP-2 may be found, for example, in Chen, et. al. "Substrate Recognition of VAMP-2 by Botulinum Neurotoxin B and Tetanus Neurotoxin," *Journal of Biological Chemistry*, 283, no. 30 (2008): 21153-21159. Tetanus neurotoxin (TeNT) also cleaves VAMP-2 at the same site as BoNT/B. Syntaxin 1a is also a SNARE protein, and is cleaved by BoNT/C.

One prominent method for detecting BoNT infection is the mouse bioassay, as described for example in Lindstrom, M., Korkeala, H., *Clinical Microbiology Reviews*, 29 (2006): 298-314. In the mouse bioassay for Botulinum Neurotoxin, large numbers of mice are infected with the sample and observed for symptoms of infection and eventual death. Although sensitive (LOD ~0.01 ng/mL of sample), this assay may require large animal populations and be quite time-consuming, often requiring >4 days.

Because of the high toxicity of Botulinum Neurotoxin, rapid diagnosis of the toxin is often important for enhanced survival rates. Additionally there are a limited number of laboratories capable of performing a mouse bioassay. While a variety of immunoassay and enzyme activity-based formats have been developed, the sensitivity and utility of these assays remains inferior to the mouse bioassay. In particular presently available assays may only provide a partial indication of the many factors ultimately linked to toxicity and best course of therapeutic intervention. For example, both light chain and heavy chain portions of the molecule are required for BoNT toxicity. In addition, BoNT complex proteins may play a critical role in systemic uptake. BoNT light chain may be present but not in the active form. Presently available assays may not distinguish between the presence of an active or inactive form of the light chain. In many cases, the BoNT serotype must be identified to properly administer therapeutics. For these reasons, comprehensive toxicity assay approaches are preferable and serotype-specific activity assays may be advantageous for effective diagnostics and therapeutic intervention.

BRIEF DESCRIPTION OF THE DRAWINGS

FIGS. 7-12 are schematic illustrations of a region of the microfluidic device of FIG. 6 during different stages of operation according to an embodiment of the present invention.

DETAILED DESCRIPTION

Figure 1:
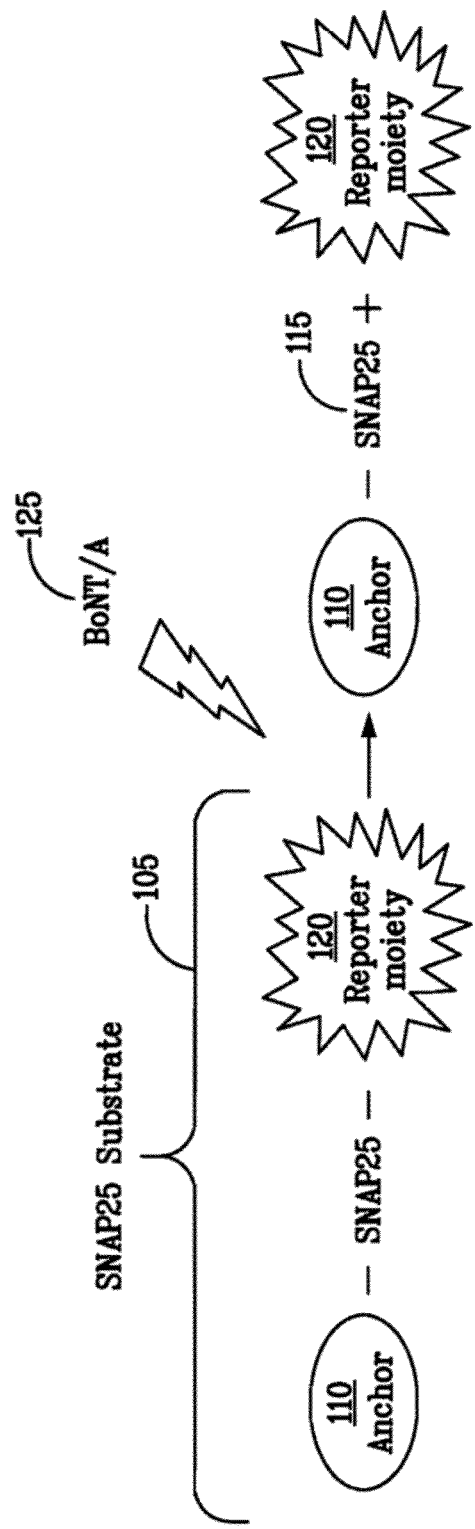
FIG. 1 is a schematic illustration of an example of the components of an assay according to an embodiment of the present invention.

Certain details are set forth below to provide a sufficient understanding of embodiments of the invention. However, it will be clear to one skilled in the art that embodiments of the invention may be practiced without one or more of these particular details. In some instances, well-known materials, chemical components, buffers or other additives, analytes, electrical components, material processing and fabrication techniques, circuits, control signals, timing protocols, and software operations have not been shown in detail in order to avoid unnecessarily obscuring the described embodiments of the invention.

As was generally described above, immunoassays for Botulinum Neurotoxin generally only detect the presence and amount of toxin proteins, and not its enzymatic activity.

Assays that do detect the presence or activity of the sample are often challenged by requirements for high sensitivity given the lethality of Botulinum Neurotoxin. Multiplexed assay platforms capable of detecting toxin proteins and activity with serotype specificity and exquisite sensitivity are most desired. Integration of multiple assays based on assay steps including metering, mixing, preconcentration, rinsing or separations, and detection in a single device that can be automated may also be advantageous. Potential advantages of such integration with microfluidic devices include faster assays, smaller sample and reagent volumes, higher sensitivity, better reproducibility, portability, labor savings, and overall cost savings.

Assays according to various embodiments of the invention utilize a substrate molecule that is cleaved by a target agent. In various embodiments, the substrate molecule includes a protein sequence, at least a portion of which may be cleaved by a target agent, such as a neurotoxin, and a reporter moiety. The substrate molecule may further include a purification tag. As will be described further below, an active target agent may cleave the protein sequence through enzymatic activity, resulting in cleaved reaction products. The cleaving affects the elution time of the reporter moiety during electrophoretic separation. Accordingly, the presence or absence of active target agent may be determined through the elution time of the reporter moiety during electrophoretic separation. The elution time may be altered by cleavage for any of a variety of reasons, including a change in charge, mass, or both. Elution time of a reporter moiety in the uncleaved substrate will generally be different than an elution time of the reporter moiety in the cleaved reaction products. In this manner, elution time of the reporter moiety may be used to determine whether or not active target had been present in a sample and active to cleave a sequence in the substrate molecule. If the target was not present, or present but not enzymatically active to cleave the protein sequence of the substrate molecule, one elution time will be observed. If the target was present and active such that the substrate molecule was cleaved, a different elution time may be observed. More detailed examples will be described below.

Assays according to embodiments of the present invention utilize a substrate molecule that may be cleaved by an active target agent. An example of the components of an assay according to an embodiment of the present invention are shown in FIG. 1. A substrate molecule 105 includes an anchor moiety 110 bound to a SNAP25 sequence 115 bound to a reporter moiety 120. The entire substrate 105 may be referred to as "intact substrate molecule". Although the entire SNAP25 sequence is shown, a portion that may be cleaved by a target agent may be used. In other embodiments, different sequences may be used, such as VAMP-2, that may be cleaved by a target agent. The sequence use may be selected to be cleaved by a target agent of interest, such as Botulinum Neurotoxin, Tetanus Neurotoxin, or other enzymatic agents.

The reporter tag can be connected to the sequence to be cleaved, and the optional purification tag can be connected to the sequence to be cleaved, directly by covalent bonds, or indirectly via a linker. The term "linker" as used herein refers to any chemical structure that can be placed between the reporter tag and sequence to be cleaved, and/or the sequence to be cleaved and purification tag.

Figure 2:
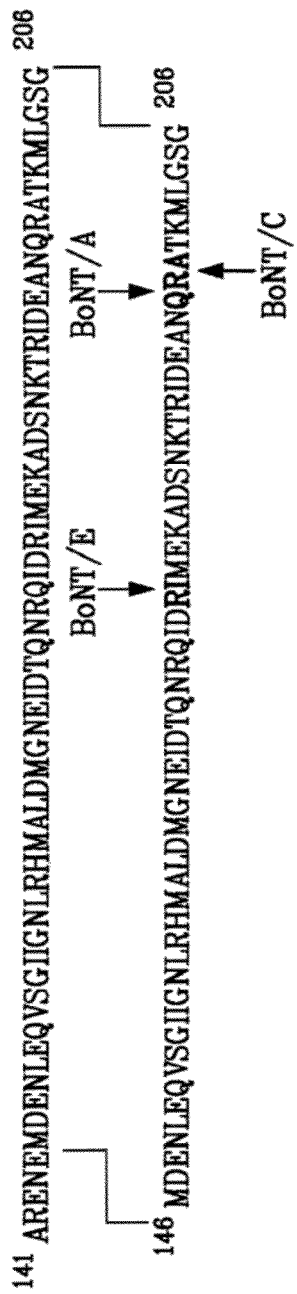
FIG. 2 is a diagram of SEQ ID NO. 1, the complete 206 amino acid sequence for SNAP25 showing the cleavage sites for BoNT/A, BoNT/C and BoNT/E, which may be used in accordance with embodiments of the present invention.

The SNAP25 sequence is provided as a sequence that will be cleaved by the target agent, Botulinum Neurotoxin A 125 in the example of FIG. 1. FIG. 2 depicts the complete 206 amino acid sequence for SNAP25 (SEQ ID NO. 1: MAEDADMRNE LEEMQRRADQ LADESLESTR RMLQLVEESK DAGIRTLVML DEQGEQLDRV EEGM- NHINQD MKEAEKNLKD LGKCCGLFIC PCNKLKSSDA YKKAWGNNQD GVVASQPARV VDEREQMAIS GGFIRRVTND ARENEMDENL EQVS- GIIGNL RHMALDMGNE IDTQNRQIDR IMEKADSNKT RIDEANQRAT KMLGSG). More information about the sequence may be found in Purcell, A. L. and Hoard-Fuchey, H. M., "A capillary electrophoresis method to assay catalytic activity of botulinum neurotoxin serotypes: Implications for substrate specificity," *Analytical Biochemistry,* 366 (2007): 207-217, which is hereby incorporated by reference in its entirety for any purpose. The enlarged portion at the bottom of FIG. 2 illustrates the cleavage sites of Botulinum Neurotoxin Types A, C, and E (BoNT/A, BoNT/C and BoNT/E), as indicated by arrows.

The reporter moiety 120 is provided to facilitate detection, as will be described further below. In various embodiments, the reporter tag can be a fluorescent tag. The fluorescent tag may exploit natively fluorescing protein sequences or domains such as green fluorescent protein (GFP). Any fluorescent tag known in the art may be used. Such fluorescent tags include, but are not limited to, GFP derivatives, such as, Red (RFP), Blue (BFP), Cyan (CFP), Yellow (YFP), Coumarin dyes, Cascade Blue, CyDyes, Fluorescein, Bodipy dyes, Rhodamine (and its derivatives), Allophycocyanin, Alexa Fluor dyes, Texas Red, Lucifer Yellow, TruRed, or Peridinin chlorophyll protein. The use of fluorescent tags may facilitate detection of enzymatic activity through the detection of a fluorescent emission, as will be described further below. In other embodiments where fluorescent detection is not used, other types of tags or reporter moieties may be used, such as tags that facilitate electronic detection. Other embodiments of reporter moieties include substrate molecules whose cleavage by an active agent results in product molecules with a detectable difference in electrophoretic mobility. This mobility difference can be detected using any suitable method, such as absorbance or colorimetric staining. That is, in some embodiments the electrophoretic mobility of cleaved reaction products, an uncleaned substrate molecule, or both, may be detected without the need for a tag. A component of the substrate molecule or reaction products may itself serve as the reporter moiety.

Referring again to FIG. 1, in the presence of active Botulinum Neurotoxin A, the SNAP25 sequence 115 is cleaved, separating the substrate molecule 105 into two portions. A first portion includes the anchor moiety 110 and the SNAP25 sequence 115. The second portion contains the reporter tag, which has been cleaved from the remainder of the intact substrate in the presence of Botulinum Neurotoxin A. The first portion may be larger than the second portion. The size difference between the smaller fluorescent portion following cleavage and the entire intact substrate prior to cleavage may be used, as described further below, to determine whether cleavage has occurred, and therefore whether the target agent was present and active.

Although a specific sequence and tags have been described with respect to FIG. 1, the sequence and tags may vary in other examples. Generally, a sequence will be provided that will be cleaved as a result of enzymatic activity of a target agent. The sequence may include a reporter moiety or may be labeled with a reporter tag to facilitate detection. In the presence of the target agent, the sequence cleaves into two or more portions. One or more of the portions may have a different electrophoretic mobility from the intact substrate molecule.

The electrophoretic mobility of one or more reaction products may then be determined, for example through an electrophoretic separation. In one example, polyacrylamide gel electrophoresis (PAGE) is used. However, performing PAGE on the 'native', or non-denatured, sample may not be suitable.

Figure 3:
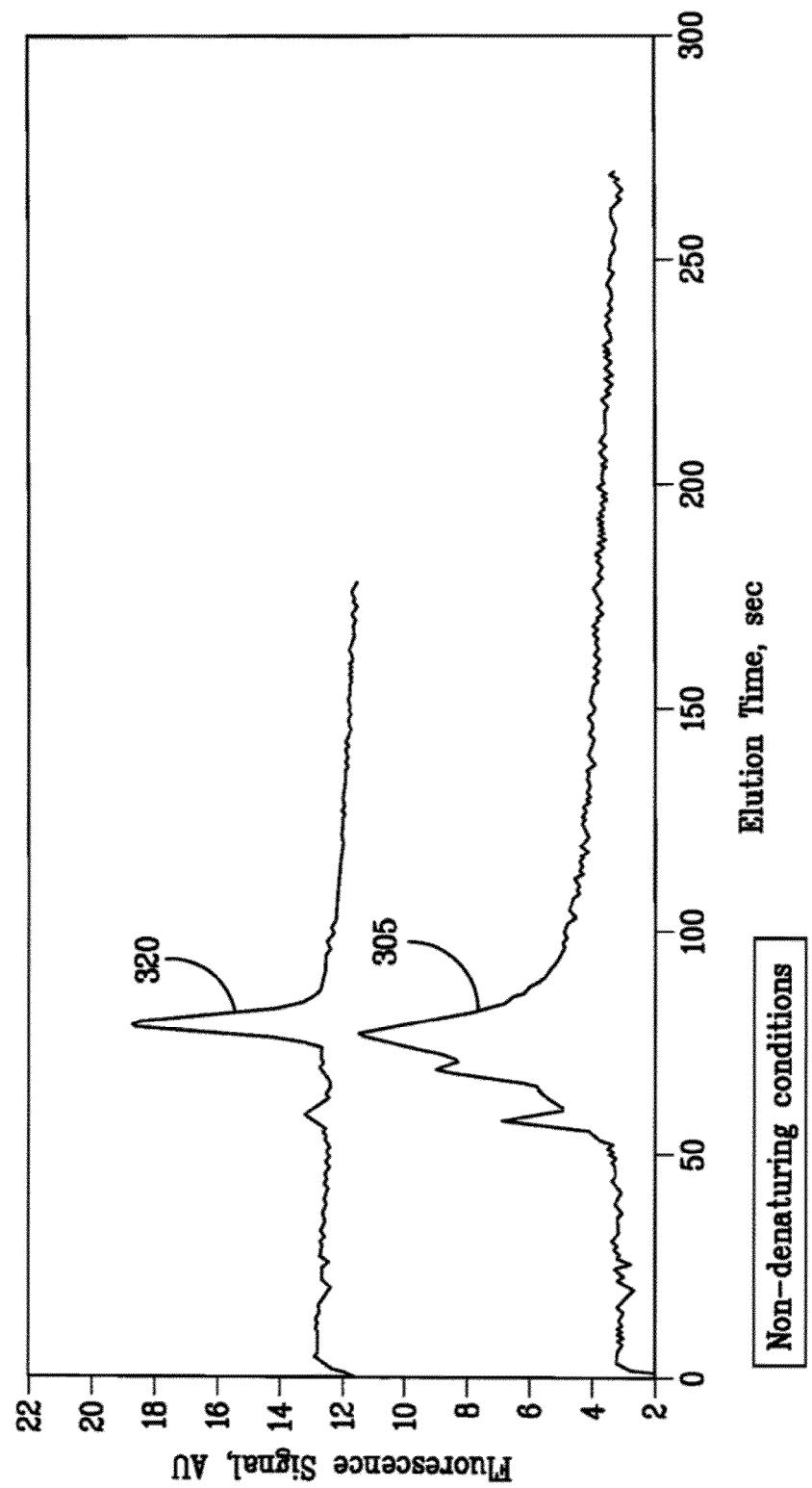
FIG. 3 illustrates the elution time for intact SNAP 25 substrate and cleaved reporter fragment under native, non-denatured conditions according to an embodiment of the present invention.

For example, FIG. 3 illustrates the elution time for the intact SNAP25 substrate molecule, such as the substrate 105 of FIG. 1, and the cleaved fluorescent portion, such as the portion 120 of FIG. 1. The graph of FIG. 3 illustrates fluorescence signal strength (AU) versus elution time in seconds.

The detected signal will generally peak as the reporter tag passes the detector. For example, when a fluorescent tag is used, the detected fluorescence will generally peak as the fluorescent tag passes the fluorescent detector. The time at which that occurs (elution time) is based on a variety of factors, including size and net charge of the species to which the reporter tag is attached.

FIG. 3 depicts detection of a fluorescent tag. Two traces are shown in FIG. 3—trace 320 and 305. Trace 320 corresponds to a sample containing intact SNAP25 substrate molecule 105 that had been exposed to 10 nM active Botulinum Neurotoxin Type A prior to PAGE. Trace 305 corresponds to a sample containing intact SNAP25 substrate molecule 105 that had not been exposed to active Botulinum Neurotoxin Type A. As can be seen in FIG. 3, both the traces 305 and 320 contain a highest peak at nearly the same elution time. Consequently, it may be difficult to identify whether the intact substrate molecule had cleaved (and therefore an active target agent was present) based on elution time. Although the fluorescent species had different sizes in the samples represented by traces 305 and 320, the non-denaturing, native conditions may have imparted charge to the species that affected their elution time.

The solution may accordingly first be mixed with a denaturant, such as sodium dodecyl sulfate (SDS), to denature the proteins and provide a more distinctive separation. Numerous denaturants are known in the art, and may also be used with suitable substrates. However, the presence of a denaturant during the time the substrate molecule is incubated with the target agent may inhibit the cleaving reaction by preventing the binding and cleaving action. Accordingly, it may be advantageous to incubate the substrate with the target agent prior to introduction of denaturant.

Figure 4:
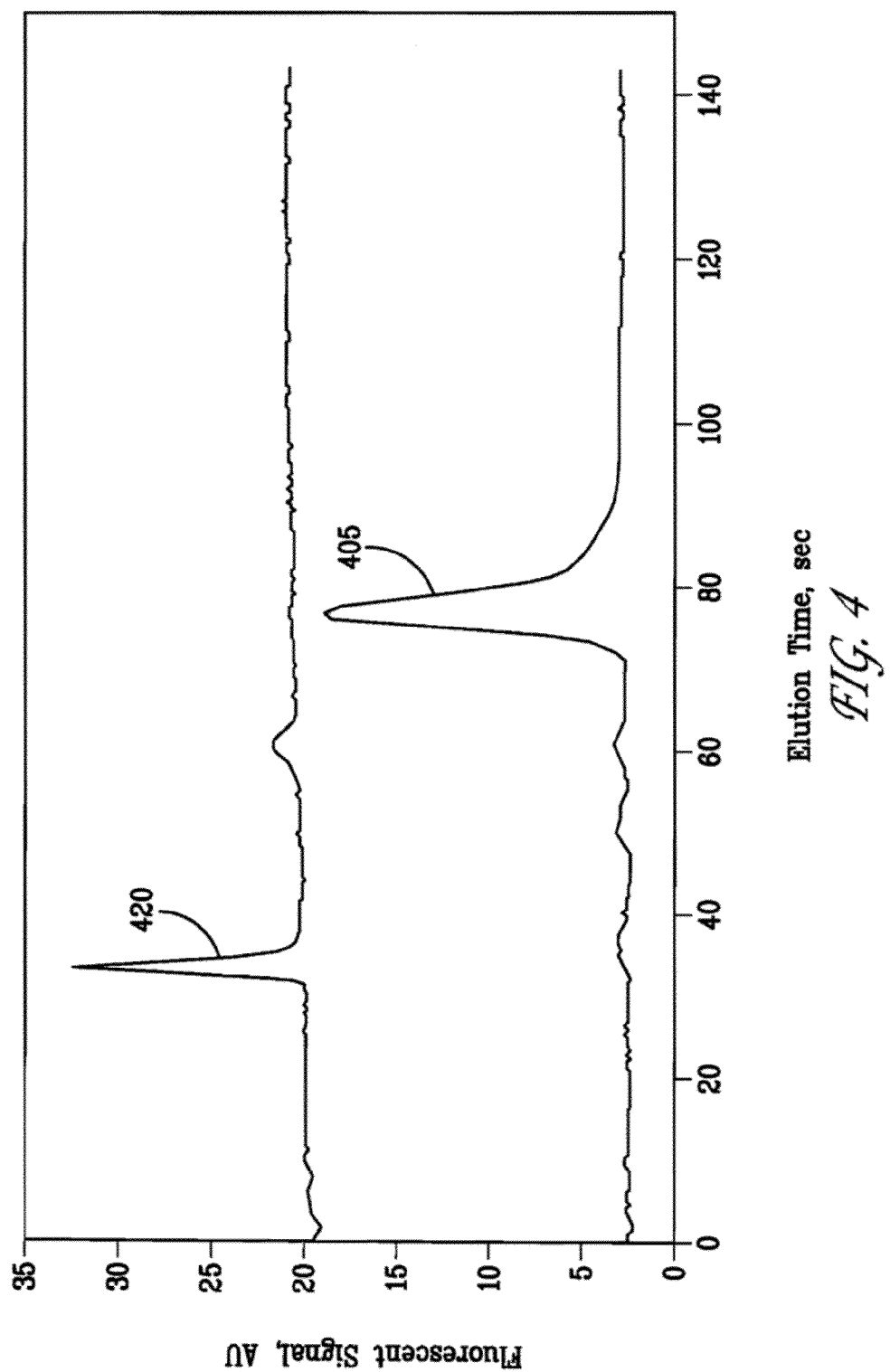
FIG. 4 illustrates the elution time for an intact SNAP25 substrate and cleaved reporter fragment under denatured conditions according to an embodiment of the present invention.

FIG. 4 illustrates fluorescent signal strength versus elution time for an assay completed using SDS-PAGE techniques to detect a SNAP25 substrate molecule incorporating a fluorescent tag. The graph shows two traces 420 and 405. Trace 420 corresponds to a sample containing intact SNAP25 substrate molecule 105, that had been exposed to 10 nM active Botulinum Neurotoxin Type A prior to SDS-PAGE. Accordingly, the reporter moiety cleaved off, as described with reference to FIG. 1. Trace 405 corresponds to a sample containing intact SNAP25 substrate molecule 105 that had not been exposed to active Botulinum Neurotoxin Type A. The fluorescent peak originated from the presence of the entire intact SNAP25 substrate molecule 105. In these SDS conditions, the difference in elution times of the peaks can be more easily detected, as shown in FIG. 4.

Figure 5:
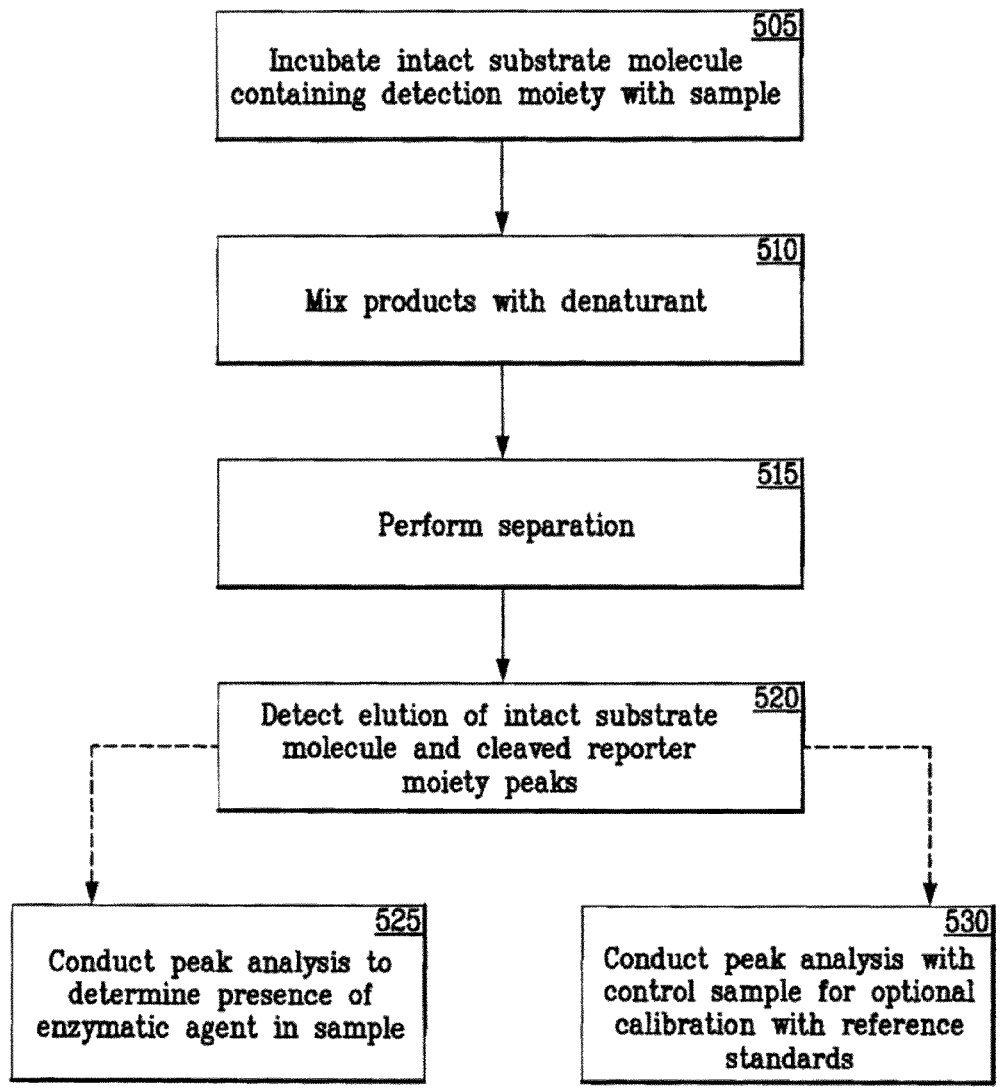
FIG. 5 is a flowchart illustrating a process for determining the presence of a target enzymatic agent in a sample according to embodiments of the present invention.

FIG. 5 is a flowchart illustrating a process for determining the presence of an active target enzymatic agent in a sample. In block 505, a substrate molecule containing a reporter moiety is incubated with a sample solution. The SNAP25 substrate molecule has been described above with reference to FIG. 1. As has been described, the substrate molecule may be designed such that it includes a protein sequence that is cleaved in the presence of an active target agent, such as the SNAP25 substrate molecule including a SNAP25 sequence being cleaved in the presence of Botulinum Neurotoxin. Other sequences may be used, such as, but not limited to, VAMP-2. Other toxins may also be detected, such as but not limited to, Tetanus Neurotoxin. The sequences that normally contain multiple different cleavage site(s) each of which is cleavable by different toxin(s) may be designed with mutations facilitating specific activity assays restricted to fewer cleavage sites, and preferably a single cleavage site specific to one toxin type. Following incubation, the solution may in some examples be mixed with a denaturant in block 510. A denaturant may be desirable, as described above, when native conditions may make discerning a cleaved product from an intact one more difficult. Separation is performed in block 515 and an elution time of the reporter moiety may be detected in block 520. Cleaved reporter moiety peaks may be generated as known in the art and results may be quantified by calculating an area or height of peaks at each elution time. Such calculation may be performed utilizing a programmed computer implementing one or more peak analysis methodologies. Results may be displayed or stored in a user or computer readable medium, such as on a display or stored in a memory. Detected elution time, peak analysis, or both, may then be correlated into the presence or absence of an active enzymatic agent in a variety of ways. In block 525, peak analysis techniques may be used to determine the presence of an enzymatic agent in the sample. The detected elution time may also be compared with a target time to determine if active enzymatic agent is present in the sample. That is, a target time may be separately established for the cleaved reaction product containing the reporter moiety, the intact substrate, or both, under the separation conditions used in the block 520. A comparison of the detected time with the target time may then yield an indication of whether the cleaved product or the entire substrate was detected, and therefore whether active enzymatic agent was present in the sample. In block 530, peak analysis may be performed on a control sample for optional calibration of the system with reference standards. The detected elution time may be compared with an elution time from a control sample to determine if an active enzymatic agent was present in the sample. The control sample may be, for example, a sample known to be exposed to the active enzymatic agent, or a sample known to not be exposed to the active enzymatic agent. By detecting a similarity or difference between the detected elution time from the sample in block 520 and the control, the presence or absence of enzymatic agent in the sample may be determined.

Having generally described assays according to embodiments of the present invention above, microfluidic devices and systems that may be used to conduct those assays will now be described. A microfluidic device typically refers to a device configured to handle fluid having one or more features on the micron or sub-micron scale. That is, a microfluidic device typically has a feature where at least one cross-sectional dimension of the features is between 0.5 μm and 500 μm. Features included in microfluidic devices may include, but are not limited to, channels, chambers, inlet and outlet ports, valves, pumps, and electrodes. The microfluidic device may be made utilizing microfabrication techniques including, for example, photolithography, wet and dry etching, and embossing.

Figure 6:
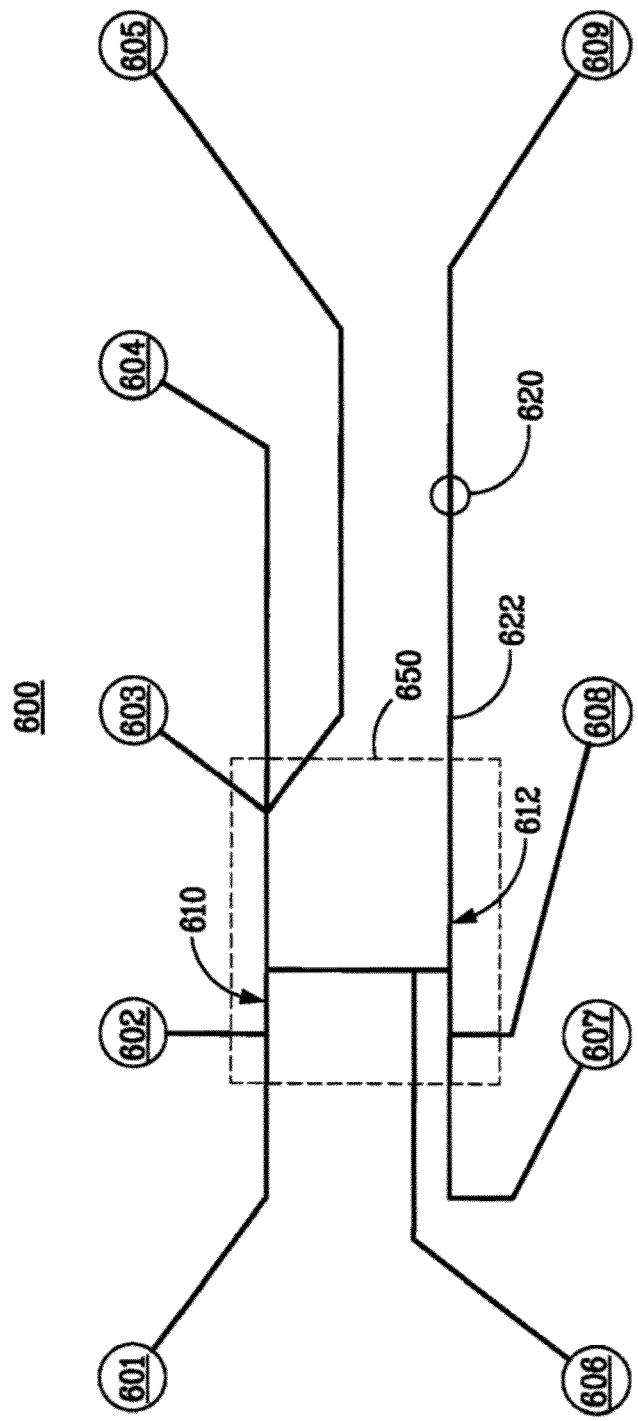
FIG. 6 is a schematic illustration of a top-down view of a microfluidic device according to an embodiment of the present invention.

FIG. 6 is a schematic illustration of a top-down view of a microfluidic device 600. Inlet/outlet ports 601-609 are provided for fluid access to the channels, represented by black lines in FIG. 6. The inlet/outlet ports 601-609 facilitate introduction or removal of fluid to and from the microfluidic device, and may be coupled to external fluid reservoirs through suitable fluidic couplings. In other embodiments, fluid reservoirs may be integrated within the microfluidic device 600. Although not visible in FIG. 6, size exclusion membranes are provided in the channels at the locations 610 and 612. The size exclusion membranes are described further below, but generally allow for the concentration of analytes in a sample, such as the intact SNAP25 substrate molecules described above, in the vicinity of the membrane. Examples of concentration of analytes at a size exclusion membrane within a microfluidic device, including methods of forming the size exclusion membranes and microfluidic device, are also described in co-pending application Ser. No. 11/536,753, filed Sep. 29, 2006, entitled "Preconcentration and separation of analytes in microchannels," which is hereby incorporated by reference in its entirety for any purpose. A detection location 620 is shown in a separation microchannel 622 in FIG. 6. A detector may be positioned to detect the presence of a reporter tag at the detection location 620. Any suitable detector may be used, including a laser-induced fluorescence detector. In some examples, the detector may be integrated with the microfluidic device 600.

The microfluidic device 600 may be fabricated using methods similar to those described in, for example, Hatch, A., et al., *Analytical Chemistry* 78 (2007): pp. 4976-4984, and Herr, A. E., et al., *Proceedings of the National Academy of Sciences* 104: (2007): 5268-5273, which are hereby incorporated by reference in their entirety for any purpose.

Any of a variety of substrates may be used to form the microfluidic device 600 including glass, fused silica, PDMS, PMMA, cyclic olefin copolymer, polycarbonate, or other material compatible with the techniques and processes described herein. In one example, photolithography is used to define the pattern for the channels shown in FIG. 6, and the channels etched into a glass substrate. In other examples, molding or embossing techniques may be used to define the channels. A second substrate containing the inlet/outlet ports 601-609 may then be bonded or otherwise adhered to the substrate containing the defined microchannels.

The channels of FIG. 6 generally may range in dimensions of depth from 1 µm to 1 mm, 1 µm to 500 µm in some embodiments, and 10 µm to 300 µm in other embodiments. The width of the microchannels generally may range from 1 µm to 1 cm, 1 µm to 1 mm in other embodiments, 1 µm to 500 µm in some embodiments, and 10 µm to 300 µm in other embodiments. The width and depth of the microchannels are generally selected to obtain the desired flow characteristics in the channels and provide sufficient volume for the amount of sample or target analytes to be received by the channel. The length of the microchannels generally may range from 10 µm to 10 cm, from 100 µm to 1 cm in other embodiments. Generally, the length of the microchannels are selected to accommodate a desired volume of sample or other fluid, distance between membranes, and length for separation in the case of the separation channel 622.

Examples of forming polyacrylamide membranes within the microfluidic device 600 will now be described. It is to be understood that the description below is by way of example only, and variations on the techniques and recipes used to form membranes at these locations may be used in other examples.

As an initial matter, surfaces of the microchannels shown in FIG. 6 may be treated with an acrylate monolayer to facilitate attachment of polyacrylamide gels to the surfaces. The acrylate monolayer may be formed using a process of incubation, rinsing, and drying. In one embodiment, the surface treatment includes conditioning one or more of the microchannels with 1M aqueous NaOH, rinsing with deionized water, and vacuum drying the microchannels. Introduction of fluids into the microchannels may occur through any known methods, including by pressure-driven or electrophoretic flow. A 2:3:5 (volume ratio) mixture of 3-(trimethoxysilyl) propyl methacrylate, glacial acetic acid, and deionized water that has been sonicated and degassed, may then be loaded into the microchannels. The microchannels may then be incubated for about 30 minutes, rinsed with a 3:7 (v/v) mixture of acetic acid and water, rinsed with deionized water, and dried with a vacuum. This process leaves an acrylate terminated self-assembled monolayer on the surfaces of the microchannels. Acrylate monolayer treatment may vary according to the substrate used, and may not be needed in some examples.

The membranes may then be polymerized within the channels at the locations shown in FIG. 6 by loading the channels with an aqueous solution including acrylamide monomer, bisacrylamide crosslinker, and a photoinitiator. The membranes may then be formed by polymerizing the solution by exposing the desired membrane area to a UV light source. One example of the quantity of acrylamide and the crosslinker bisacrylamide are listed as a total concentration percentage (T) and a concentration of the crosslinker (C), which can be calculated using the following equations:

$$\% \text{ Total } (T) = \frac{\text{g } (acryl + bis)}{100 \text{ mL}}, \% \text{ Crosslinker } (C) = \frac{\text{g } bis}{100 \text{ g } (acryl + bis)}$$

For the membranes at the locations 610 and 612 in FIG. 6, a solution of 40% T and 12% C 0.2% photoinitiator (such as VA-086) may be used. The membranes may be polymerized by exposure to a shaped energy source, such as a laser beam, or the device may be masked to expose only the desired regions of the device during a more blanket exposure to the energy source. The resultant polymerized membrane may fill the entire cross-section of the respective channel at the locations 610 and 612 and have a length that is determined by the area exposed to the energy source. Unpolymerized solution may then be removed from the device.

Polymerized membranes within the microfluidic device may be utilized in one or more steps of the described assay procedures, including but not limited to concentration of the substrate molecule and sample, incubation to generate reaction products, and incubation with a denaturant to create separation conditions that are different from the reaction conditions. The substrate molecules, sample agent, reaction products, or combinations thereof may be concentrated at one or more size-exclusion membranes during assays described herein. The concentration generally proceeds by driving the substrate molecules, sample agent, or reaction products towards the membrane using an electric field. Membranes may accordingly be used which are size-exclusive for the enzyme, substrate molecules, and reaction products that fall above a certain size threshold. The electric field strength and membrane composition may be selected to achieve size-exclusion above a relevant threshold for the molecules being concentrated.

For typical size-exclusion membrane conditions in which the buffering capacity of the membrane is less than the buffering capacity of the surrounding gel or buffer solution, the enzyme, substrate molecule, and reaction products may need to be larger than about 10 kDa for effective concentration at the membrane. In some examples, the substrate molecule and reaction products may need to be larger than 25 kDa for concentration at the membrane. Referring back to FIG. 1, the SNAP25 substrate molecule 105 may accordingly have a size greater than about 30 kDa, and in some examples greater than about 50 kDa. The reaction products including the portion containing the anchor 110 and the portion containing the reporter moiety 120 may each have a size greater than about 15 kDa, and in some examples greater than 25 kDa. Additionally, the size-exclusive properties may be affected by the electric field strength applied across the membrane. If an applied field is too large, the reaction products or substrate molecules may nonetheless be driven into the membrane. For example, an electric field strength across the neutral membrane of less than 50 V/cm should generally be used to concentrate molecules of a size between 10-25 kDa, and in some examples a field strength of less than 30 V/cm may be used. For larger molecules (such as 26-75 kDa), an electric field strength less than 80 V/cm across the membrane may be used, and may in some examples an electric field strength less than 50 V/cm may be used. For larger molecules (>75 kDa), an electric field strength less than 200 V/cm may be used, and in some examples an electric field strength less than 100 V/cm may be used. For the above conditions, the total monomer percentage used in fabricating the neutral size-exclusion membranes may need to be greater than 20% T and 2.5% C, and may in some examples need to be greater than 30% T and 5% C.

Smaller molecules (such as those 0-25 kDa) may require a membrane with immobilized charge or buffering groups to control the local pH of the membrane such that it is less than the isoelectric point (pI) of the molecule. The pH of the membrane may be between pH 1.0 and the pI of the molecule(s), and generally should be no greater than 1 pH unit less than the pI of the molecule(s), and may be 2 pH units less than the pI of the molecule(s). The pH of the membrane may generally be controlled by introducing calculated amounts of acrylamido buffers (such as IMMOBILINE®) into the aqueous acrylamide monomer solution. Various embodiments of suitable aqueous solutions and methods for polymerizing acrylamide gel regions are described in co-pending application Ser. No. 12/182,755, filed Jul. 30, 2008, entitled "Methods for Providing and Using Solution Gradients in Microchannels," as well as Ser. No. 12/243,817, filed Oct. 1, 2008, entitled "Devices, Systems, and Methods for Microscale Isoelectric Fractionation", the entire contents of which are hereby incorporated by reference for any purpose. The buffering capacity of the membrane may need to be greater than the buffering capacity of the local solution phase buffers within the system, or of the sample(s) loaded onto the device, and may need to be 10 times greater than the buffering capacity of the local solution phase buffers within the system, or of the sample(s) loaded onto the device. If the buffering capacity of the charged membrane is too low, the local pH may be shifted such that substrate or fragments are not effectively excluded. A membrane pH may not be too much lower than 1 to 2 pH units below the lowest pI for substrate and fragments to be excluded. Lower membrane pH may require higher concentration of immobilized negative charge which may result in undesirable concentration polarization at the membrane thereby limiting reproducibility and utility of the membrane for mixing, preconcentration and integrated separations. Membranes contributing to local pH that is too low or too high may also inhibit enzymatic activity near the membrane and the membrane pH may be adjusted accordingly in order to optimize both exclusion and activity. The substrate molecule and cleaved fragments may also be engineered to have pI that are effectively excluded at pH where enzyme has higher activity. If requirements for membrane pH, substrate and fragment pI, and pH range of toxin activity cannot be met, a neutral membrane and suitable substrate molecule and conditions described above may be used. The electric field strength applied across the membrane for the above conditions may be less than 300 V/cm, and in some examples may be less than 100 V/cm. Additionally, for the above conditions, the total monomer percentage used in fabricating the membranes may be greater than 5% T and 2.5% C, and may in some examples be greater than 20% T and 5% C. The above descriptions may apply to proteins, peptides, or related molecules of similar mechanical and chemical properties, and may need to be adjusted for other molecules, such as DNA and RNA, if properties such as charge are a dominant factor.

Referring again to FIG. 6, a gel may also be formed in the separation channel 622 to facilitate electrophoretic separations. The solution used to form the separation gel may have a different composition than that used to form the membranes at locations 610 and 612. In one example, the separation gel is formed using an aqueous solution of 8% T and 2.6% C. Following exposure to an energy source to polymerize the separation gel, unpolymerized solution may be removed from the device.

In some examples, gels may be formed in other regions of the device, including throughout the channels shown in FIG. 6. These gels may be formed using a different composition than those used to form the membranes at locations 610 and 612 or the separation gel. In one example, a solution of 3.5% T and 2.6% C may be used. If the device is to be stored prior to use, a buffer solution may be placed in the channels to avoid damaging the polymerized gels. While the gels fill the cross-sectional area of the channel, they generally all have pore sizes large enough to facilitate bulk fluid flow through the device. The membranes polymerized at the locations 610 and 612 are designed to have pore sizes that will exclude the substrate sequence, described above, such that the substrate molecule may be concentrated at the membrane locations 610 and 612, as will be described further below.

FIGS. 7-12 are schematic illustrations of the region 650 of the microfluidic device of FIG. 6 during different stages of operation. The membranes 715 and 720 are shown in the areas corresponding to locations 610 and 612 of FIG. 6. Example electrode configurations for electrophoretic transport of fluid are also shown in FIGS. 7-12. The electrode configurations are by way of example only and different configurations may be used to affect electrophoretic transport, or other transport mechanisms not requiring electrodes may be used in other examples, such as pressure-driven flow.

Figure 7:
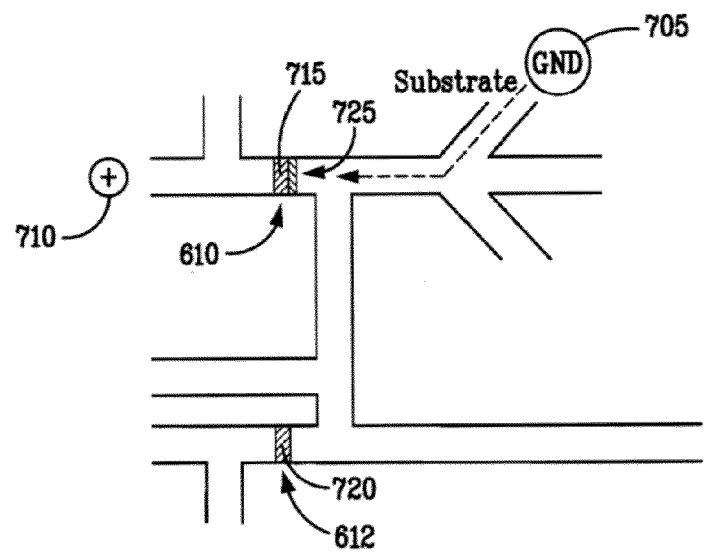

FIG. 7 schematically illustrates loading of a substrate molecule including a protein sequence to be cleaved by an active target agent, such as the intact SNAP25 substrate molecule described above. The complex may be stored in a reservoir, and by applying a potential difference between an electrode 705 associated with a region containing the substrate sequence, and the electrode 710 positioned at an opposite side of the membrane 715 from the substrate reservoir, the substrate sequence molecules may be transported toward the membrane 715. The electrode 705 may be integrated with the microfluidic device, or positioned to generate a potential in or near the illustrated portion of the microfluidic device. Because of the pore size of the membrane 715, the substrate sequence, such as the intact SNAP25 substrate complex, may not pass through the membrane 715, and may accordingly be concentrated at a region 725 adjacent the membrane 715.

Figure 8:
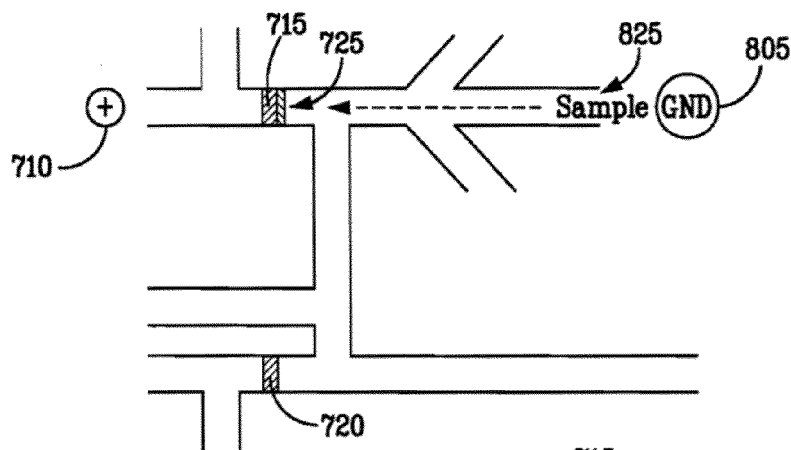

FIG. 8 schematically illustrates the introduction of a sample fluid into the microfluidic device. A sample fluid may be introduced to the device by applying a potential difference between electrode 805 disposed in a region 825 containing the sample fluid and the electrode 710 on the opposite side of the membrane 715. Generally any type of sample may be used, including sample fluids containing any type of biological fluid sample. A powder, solid, or gaseous sample may be prepared into a liquid sample in any of a variety of ways known in the art, and introduced into the microfluidic device. The assay being conducted tests for the presence of an active target agent, such as Botulinum Neurotoxin or Tetanus Neurotoxin, and accordingly, the sample may generally be any sample for which there is a desire to know if the sample contains the active target agent. In some examples, the sample may be a control sample that is either known to contain, or known not to contain the active target agent. Referring again to FIG. 8, analytes in the sample may be drawn toward the preconcentrated substrate sequence in region 725 and also preconcentrated near the membrane 715.

While the above description provides for concentration of the substrate molecule followed by introduction of the sample, in other examples, the sample may first be concentrated at the membrane 715, followed by introduction of the substrate molecules. In still other examples, the substrate molecule and the sample may be introduced to the device and concentrated near the membrane 715 at around the same time.

Figure 9:
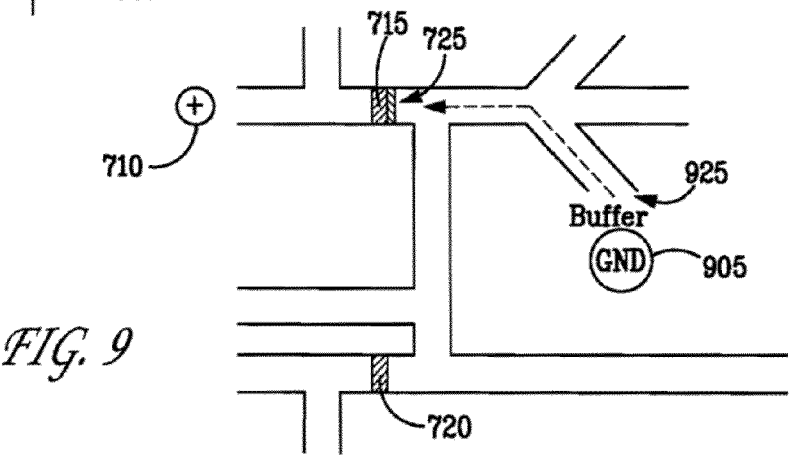

An incubation time may then pass during which time the sample and the substrate sequence may interact and mix. Any active target agent concentrated near the membrane 715 in region 725 may cleave the substrate molecule during this time. In some examples, the device may be heated or cooled during the incubation time. FIG. 9 is a schematic illustration showing the loading of a buffer solution into the microfluidic device during the incubation time to ensure that the substrate sequence and sample fluid remain in the vicinity of the membrane 715. Buffer may be drawn toward the membrane 715 by applying a potential difference between an electrode 905 disposed in a region 925 containing the buffer fluid and the electrode 710 on an opposite side of the membrane 715. The force of the buffer fluid flowing in the direction indicated may generally ensure that the substrate sequence and sample species remain concentrated at the vicinity of the membrane 715. The incubation time may vary according to the sample, substrate molecule, and any heat applied; however in one example, the incubation time for the intact SNAP25 substrate molecule and a sample containing Botulinum Neurotoxin may be less than three minutes.

FIG. 10 is a schematic illustration showing transport of reaction products from the membrane 715 to the membrane 720. By applying a potential difference between the electrode 710 and an electrode 1005 positioned on an opposite side of the membrane 720 from the reaction products, the reaction products may be transported from the membrane 715 to the membrane 720 through the transport channel 1012. The buffer or sample solution containing the reaction products is drawn through the membrane 720 while the reaction products are excluded by the pores in the membrane 720, and concentrate in the vicinity of the membrane 720 at a location 1015. If an active target agent (such as Botulinum Neurotoxin) had been present in the sample, it may have cleaved the relevant sequence of the substrate molecule. Accordingly, the reaction products may include the cleaved reporter moiety and a second portion unconnected from the reporter moiety, as described above with reference to FIG. 1. If the active target agent was not present in the sample, or not active, the substrate molecule may not have been cleaved, and the reaction products may include the intact substrate molecule, still containing the reporter moiety.

FIG. 11 is a schematic illustration showing introduction of denaturant, such as SDS, into the microfluidic device. An SDS solution may be electrophoretically loaded into the device by applying a potential difference between the electrode 1005 and an electrode 1105 located in a region 1125 containing the SDS solution. Bringing the SDS solution into the location 1015 of the reaction products allows denaturation to begin. The denaturation process may continue for as long as necessary, and typically less than four minutes is sufficient.

In this manner, a substrate sequence may be concentrated at one membrane and exposed to a solution that may contain a target agent. Enzymatic activity may accordingly take place in the vicinity of that membrane, membrane 715 with reference to FIG. 11. The reaction products may be transported to a different membrane and exposed to an SDS solution. By incubating the sample with the target sequence in a location separate from the region 1110 where SDS is introduced, any possible enzymatic activity by a target agent in the sample may be unaffected, or less affected, by the presence of SDS. By introducing an SDS solution through a side channel 1112 in FIG. 11, any residual presence of SDS in the vicinity of the membrane 715 where enzymatic activity occurs may be reduced. That is, the device configuration and process described above with regard to FIGS. 7-11 may allow for a user to conduct an assay of the type described above with regard to FIGS. 1-5 where SDS is introduced to the reaction products in a separation location from where enzymatic activity is taking place.

FIG. 12 is a schematic illustration of a start of a separation process within the microfluidic device. The reaction products, having been concentrated at the membrane 720 and denatured by the presence of SDS, may be separated along the separation channel 622 by performing SDS-PAGE, which may involve the application of a potential between the electrodes 1005 and 1205 at opposite ends of the separation channel 622. In this manner, the reaction products may be separated as they are passed along the separation channel 622 and a reporter tag detected at the downstream detection region 620 (shown in FIG. 6). As has been described above, the elution time until detection of the reporter tag at the detection region may indicate whether enzymatic activity has taken place, and therefore whether active target agent was present in the sample.

Embodiments of a microfluidic device have been described above utilizing two membranes. Substrate molecules are concentrated in the vicinity of a first membrane as are analytes from a sample. Enzymatic activity may occur to cleave the substrate molecules at the first membrane. Reaction products may then be concentrated at a second membrane and exposed to a denaturant prior to electrophoretic separation.

Figure 13:
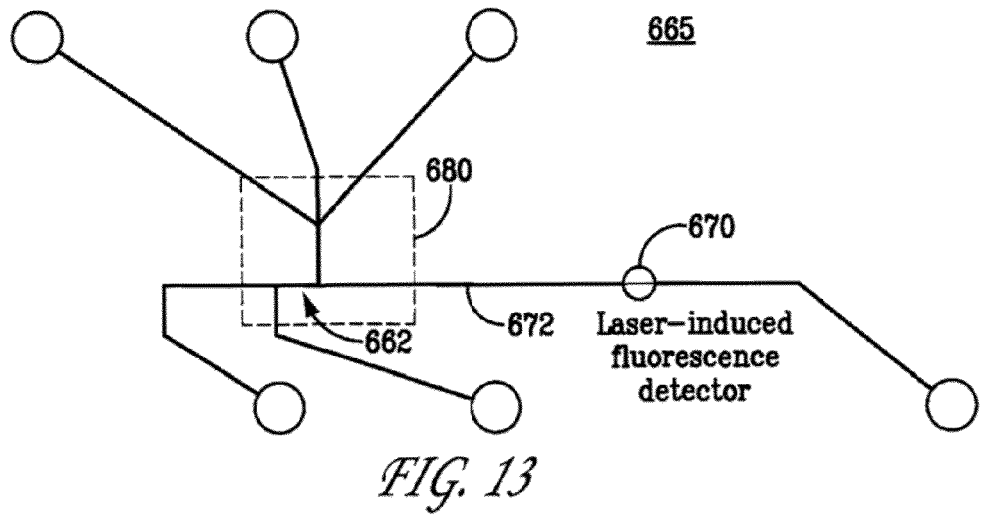
FIG. 13 is a schematic illustration of a top-down view of a microfluidic device according to an embodiment of the present invention.

In some embodiments, a denaturant may not be required, or the presence of the denaturant may not prohibitively affect the activity of the target enzyme. Accordingly, a one-membrane microfluidic device may be used in some examples. FIG. 13 is a schematic illustration of a microfluidic device 665 including a membrane in a region 662. As was generally described above, substrate molecules and target agents from a sample may be concentrated in the vicinity of the membrane in the region 662. An electrophoretic separation of the reaction products may then be performed in the separation channel 672, and an elution time of a reporter moiety measured in a detection region 670.

Figure 14:
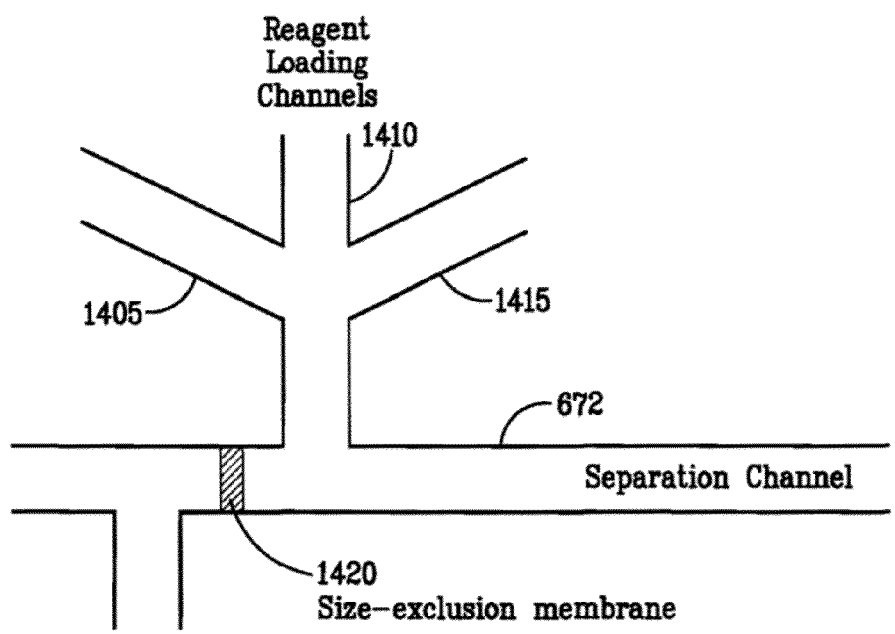
FIG. 14 is a schematic illustration of a portion of the microfluidic device of 13 according to an embodiment of the present invention.

FIG. 14 is a schematic illustration of region 680 of the device of FIG. 13. Reagent loading channels 1405, 1410 and 1415 are connected to the separation channel 672. A size-exclusion membrane 1420 is positioned at an opposite end of the fluid entry to the separation channel 672 from the detection region. During operation, substrate molecules may be concentrated at the membrane 1420 from the loading channel 1405. A sample may be loaded, and target agents concentrated at the membrane 1420 from the loading channel 1410. Buffer solution may be loaded and drawn toward the membrane 1420 from the channel 1415 to maintain a concentration of substrate molecules and target agent during an incubation time. Reaction products may then be separated in the separation channel 672. As generally described above, concentration can be achieved through the use of properly placed electrodes and potential differences.

Figure 15:
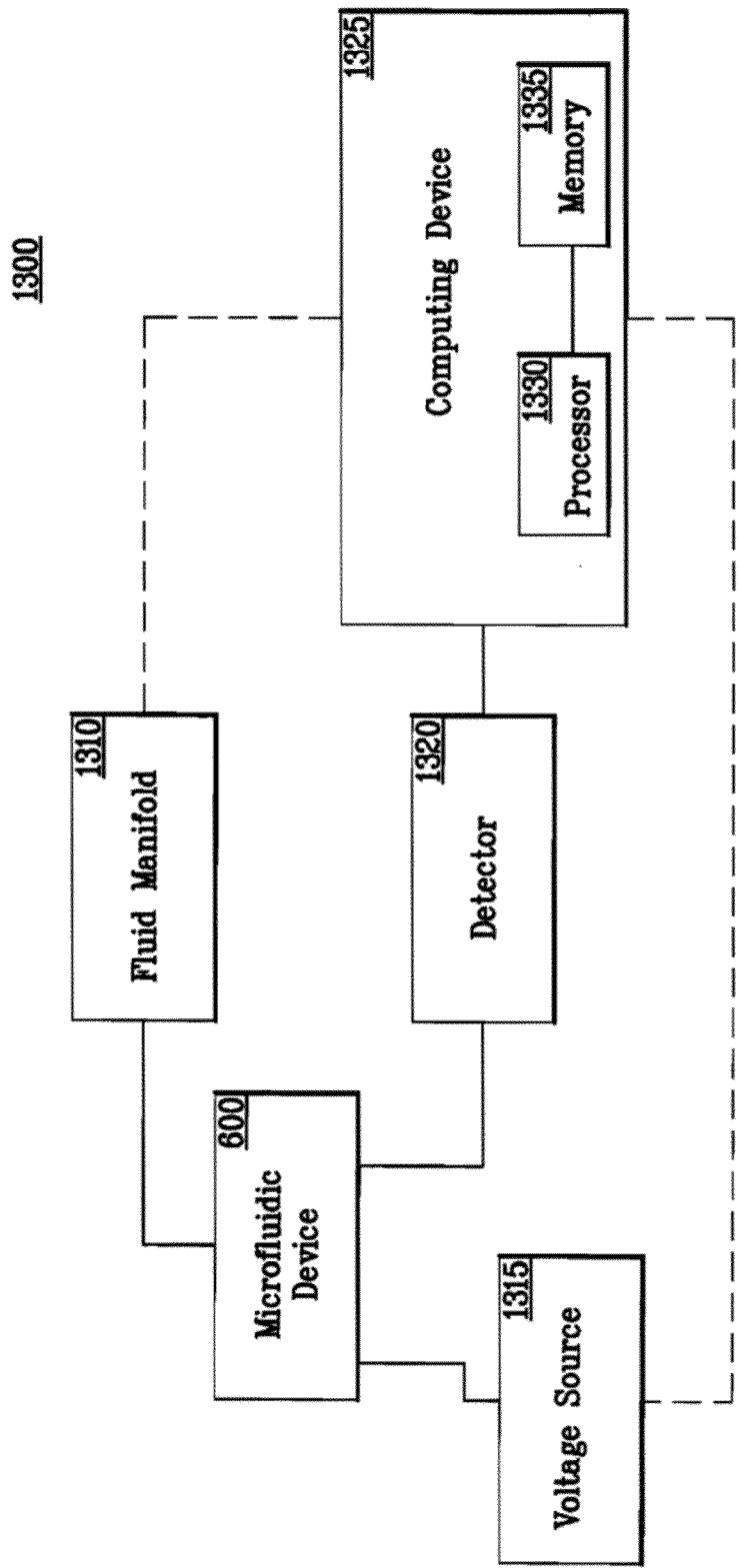
FIG. 15 is a schematic illustration of a system according to an embodiment of the present invention.

FIG. 15 is a schematic illustration of a system 1300 including the microfluidic device 600. The system 1300 includes a fluid manifold 1310, a voltage source 1315, a detector 1320, and a computing device 1325. The fluid manifold may include a variety of reservoirs coupled to the microfluidic device 600 through the inlet/outlet ports 601-609 shown in FIG. 6. The fluid manifold may further include valves, pressure, or other controls, to regulate the flow of fluids out of or into their respective reservoirs. A voltage source 1315 is provided to generate the potential differences discussed with reference to FIGS. 7-12. The voltage source may be coupled to the described electrodes which may be integrated with, or separate from, the microfluidic device 600. The detector 1320 is positioned to detect the presence of the reporter tag in the detection region 620 of the microfluidic device. Any of a variety of detectors may be used in accordance with the type of reporter tag used. Examples of the detector 1320 include, but are not limited to, a laser-induced fluorescence detector, a CCD-based fluorescence detector, a UV absorbance detector, and an electrochemical detector, such as those described in Wang, J., *Talanta*, 56 (2002): 223-231, which is hereby incorporated by reference in its entirety for any purpose.

A computing device 1325 may also be provided that may include a processor 1330 and a memory 1335. The computing device 1325 may be coupled to the detector 1320 and configured to determine an elution time until detection of the reporter tag, or receive a signal indicative of the elution time from the detector 1320. The memory 1335 may store a known target time, described above with reference to FIG. 5, and the computing device 1325 may be configured to perform the comparisons described with reference to FIG. 5 to determine if an active target agent was present in a sample introduced to the microfluidic device 600. The computing device 1325 may additionally be coupled to the fluid manifold 1310, the voltage source 1315, or both, to control the fluid flow process described above with reference to FIGS. 7-12. The memory 1335 may encode computer executable instructions that, when executed, cause the processor 1330 to couple control signals to the voltage source 1315, fluid manifold 1310, detector 1320, or combinations thereof, to accomplish the assays described above.

From the foregoing it will be appreciated that, although specific embodiments of the invention have been described herein for purposes of illustration, various modifications may be made without deviating from the spirit and scope of the invention.

What is claimed is:

1. A microfluidic device for detection of an active enzymatic agent, the device comprising:
   a substrate defining at least a portion of a first channel, a second channel, and a third channel coupled between the first channel and the second channel;
   a first membrane positioned in the first channel and configured to block a substrate molecule including a reporter moiety and a sequence configured to be cleaved by the active enzymatic agent;
   at least one reagent loading channel coupled to the first channel, the third channel coupled to the first channel at a location between the reagent loading channel and the first membrane;
   a second membrane positioned in the second channel and configured to concentrate reaction products generated following exposure of the active enzymatic agent to the substrate molecule; and
   wherein the third channel is configured to transport reaction products from a vicinity of the first membrane to a vicinity of the second membrane; and
   a separation channel including a separation gel, the separation channel coupled to the second channel and configured for separation of the reaction products, an elution time of the reporter moiety to a detection region in the separation channel being indicative of presence or absence of the active enzymatic agent in the sample.

2. The microfluidic device of claim 1 wherein the first membrane comprises a polyacrylamide membrane.

3. The microfluidic device of claim 1 further comprising a first pair of electrodes positioned to generate electrophoretic transport across the first membrane.

4. The microfluidic device of claim 1 wherein the active enzymatic agent comprises Botulinum Neurotoxin.

5. The microfluidic device of claim 1 wherein the active enzymatic agent comprises tetanus Neurotoxin.

6. The microfluidic device of claim 1 wherein the sequence comprises a SNAP25 sequence.

7. The microfluidic device of claim 1 wherein the sequence comprises a VAMP-2 sequence.

8. The microfluidic device of claim 1 further comprising a second pair of electrodes positioned to generate electrophoretic transport across the second membrane.

9. The microfluidic device of claim 1 further comprising a fourth channel coupled to the third channel and configured to deliver a denaturing agent to a vicinity of the second membrane.

10. The microfluidic device of claim 9 further comprising a pair of electrodes positioned to transport the denaturing agent in electrophoretic flow toward the second membrane and away from the first membrane.

11. The microfluidic device of claim 1 wherein the reporter moiety comprises fluorescent tag.

12. The microfluidic device of claim 1 wherein the reaction products include a cleaved portion of a SNAP25 sequence including the reporter moiety and a second portion of the SNAP25 sequence not including the reporter moiety, the cleaved portion being smaller than the second portion.

13. The microfluidic device of claim 1 wherein the first membrane has a pore size selected to exclude the substrate molecule.

14. The microfluidic device of claim 1 wherein the first membrane has a first side, and wherein the at least one reagent loading channel is configured to deliver the substrate molecule and the sample fluid to the vicinity of the first side of the first membrane, and wherein the third channel is configured to transport reaction products from the vicinity of the first side of the first membrane to a vicinity of the second membrane.

15. The microfluidic device for detection of an active enzymatic agent of claim 1, wherein the separation gel is different from the first membrane and the second membrane.

* * * * *